United States Patent

Black et al.

[11] Patent Number: 6,095,967
[45] Date of Patent: Aug. 1, 2000

[54] ISOTOPE SEEDING SYSTEM THAT RELEASES RADIOACTIVE SEEDS FOR TREATMENT OF CANCEROUS CELLS

[75] Inventors: Wayne J. Black, Vancouver, Wash.; Manfred Mittermeier, Northfield, Ill.

[73] Assignee: Manan Medical Products, Inc., Northbrook, Ill.

[21] Appl. No.: 09/047,715

[22] Filed: Mar. 25, 1998

[51] Int. Cl.[7] .................................................. A61M 36/00
[52] U.S. Cl. .................................. 600/7; 604/57; 604/59; 604/60
[58] Field of Search ............................. 600/7, 8; 604/57, 604/59, 60, 61, 62, 63, 64, 44, 20

[56] References Cited

U.S. PATENT DOCUMENTS 4,610,242  9/1986  Santangelo et al. .................... 600/114

OTHER PUBLICATIONS

1. Promotional one page brochure entitled *Prostate Seeding Set*, Mar. 1990 by Manan Medical Products, Inc.
2. Manan Medical Products, Inc.'s specification drawing for the Prostate Seeding Set hub, shown in its promotional flyer of item 1 above.

*Primary Examiner*—Linda C. M. Dvorak
*Assistant Examiner*—R. Kearney
*Attorney, Agent, or Firm*—Dick and Harris

[57] ABSTRACT

An isotope seeding system that controls the release of radioactive seeds for treatment of cancerous cells during cancer treatment procedures. The isotope seeding system comprises at least one seed that is chargeable with radioactive isotopes. At least one dissolvable web netting may alternatively be positioned about the at least one seed, and a seed deployment assembly is utilized for delivering the at least one seed, with or without the dissolvable web netting, into an organism's tissue, to surround cancerous cells. The seed deployment assembly includes an elongated cannula, a hub assembly and an obturator. The hub assembly includes an initial inner diameter at its proximal end and an operable length between the proximal end of the hub assembly and the proximal end of the cannula, the ratio of the initial inner diameter relative to the operable length being in the range of 0.075 to 0.175, to preclude against jamming of the at least one seed, with or without the at least one dissolvable web netting wrapped thereabout, within the hub assembly and/or to further preclude against inadvertent migration of such seeds from the web netting when such netting is utilized.

16 Claims, 1 Drawing Sheet

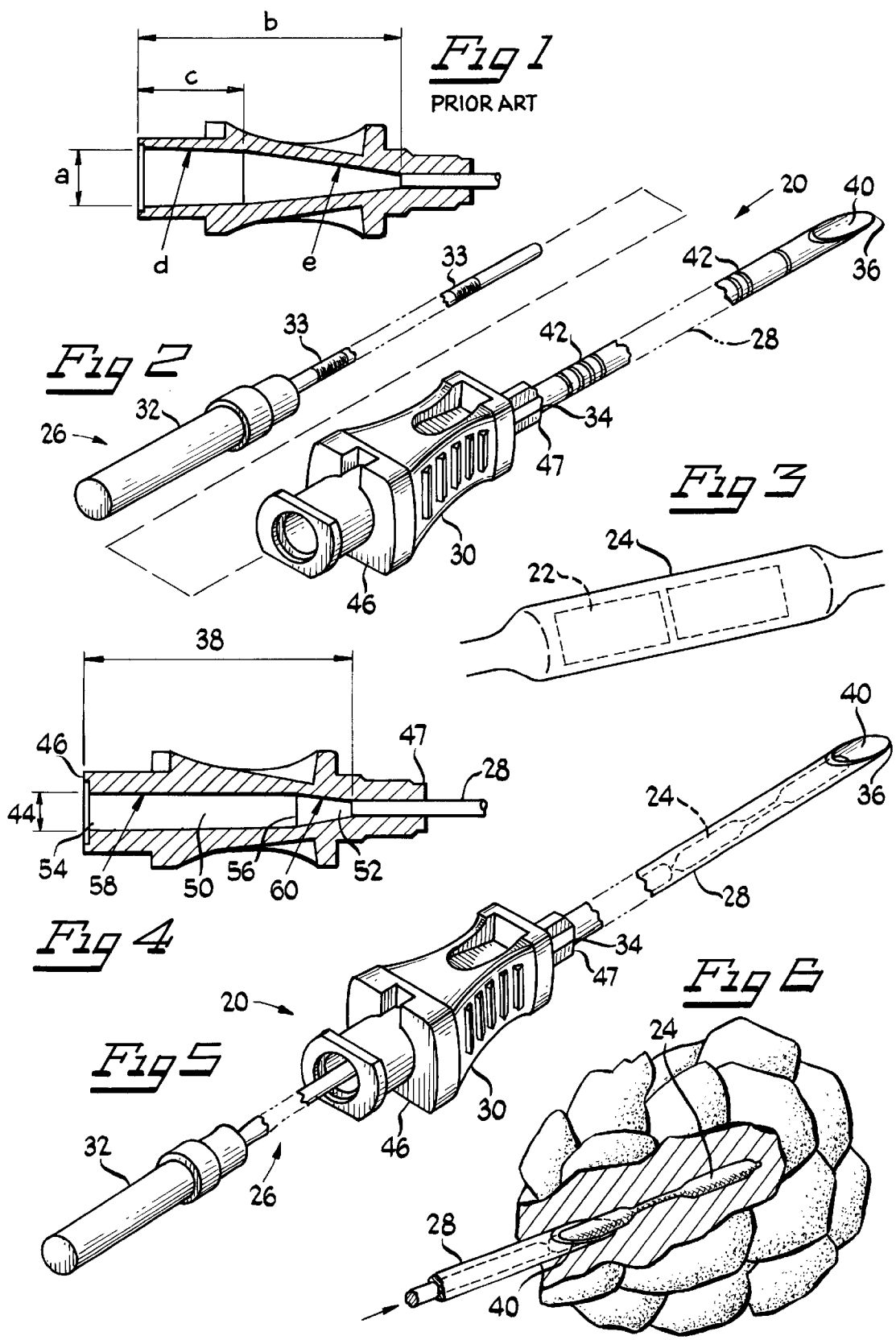

ISOTOPE SEEDING SYSTEM THAT RELEASES RADIOACTIVE SEEDS FOR TREATMENT OF CANCEROUS CELLS

BACKGROUND OF THE DISCLOSURE

The present invention is directed to an isotope seeding system that controls the release of radioactive seeds for treatment of cancerous cells during cancer treatment procedures, such as prostate surgery.

The implantation of radioactive seeds, such as iodine, for the treatment of cancer, particularly prostate cancer, is well-known in the art. Traditionally, isotope seeding systems (as shown in FIG. 1) have comprised an obturator, a hub assembly, and a cannula. The customary open seeding technique was used to dispense seeds around cancerous cells. However, individual seeds often move slightly after leaving the rigid confines of a needle, and accordingly, precise alignment of seeds has often been difficult to achieve.

To reduce the migration of seeds, ultrasound-guided radioactive seed implantation, using devices such as the I-125 Rapid Strand™ supplied by Medi-Physics, Inc., has been developed. In such prior art devices, radioactive seeds have been embedded in a somewhat stiffened, dissolvable vinyl carrier. The specified number of seeds are then implanted in a linear fashion during needle withdrawal. As a result, seed migration has been minimized. However, prior art devices, such as the one shown in FIG. 1, have not always resulted in the optimal linear arrangement of radioactive seeds around cancerous cells, since some seeds become misaligned and/or released from the vinyl carrier while still in the hub. Moreover, such prior art configurations may result in jamming of the radioactive seeds and/or the dissolvable web nettings within the hub during cancer treatment procedures. Jamming of the radioactive seeds can occur in the hub regardless of whether the radioactive seeds are freely located within the hub or preliminarily positioned within the dissolvable web nettings.

In FIG. 1, which illustrates a prior art system, "a" represents the initial inner diameter of the hub assembly, which, for example, can be 0.168 inches, and "b" represents the operable length of the hub assembly, which, for example, can be 0.745 inches. Moreover, "c" is the length of the first conical section, which can typically be 0.3 inches, while "d" is the slope from the proximal end to the distal end of the first conical section, which is approximately 1°43'06". Further, "e", the slope from the proximal to the distal end of the second conical section, is approximately 7°. However, these prior art dimensions, and subsequent configuration, can result in the premature release of radioactive seeds from within the wrapped vinyl carrier in the hub assembly; prior to transmission through the cannula and release into the organism's tissue that surrounds cancerous cells. Additionally, regardless of whether the radioactive seeds are first enveloped in the wrapped vinyl netting, such prior art dimensions may cause radioactive seeds to become jammed within the hub assembly during cancer treatment procedures.

It is therefore an object of the present invention to reduce radiation exposure during cancer treatment procedures by more efficiently dispensing radioactive seeds into an organism's tissue;

It is also an object of the present invention to prevent the premature release of radioactive seeds from the dissolvable web netting in the hub assembly during cancer treatment procedures and to prevent the jamming of such seeds in the hub assembly regardless of whether they are freely located or wrapped in dissolvable web netting;

It is a further object of the present invention to maximize the amount of appropriately wrapped or unwrapped radioactive seeds for release around cancerous cells during cancer treatment procedures;

It is yet another object of the present invention to minimize the amount of healthy, non-cancerous tissue that is damaged by either radioactive seeds that have migrated free of wrapped netting during cancer treatment procedures or from jammed radioactive seeds that have been deformed;

It is a further object of the present invention to prevent jamming of the radioactive seeds and/or the dissolvable web netting within the hub assembly during cancer treatment procedures.

These and other objects of the invention will become apparent in light of the present specification, claims and drawings.

SUMMARY OF THE INVENTION

The invention comprises an isotope seeding system that controls the release of radioactive seeds for treatment of cancerous cells to preclude against jamming and inadvertent migration of the radioactive seeds, with or without dissolvable web nettings within the hub assembly, during cancer treatment procedures. The system includes at least one seed that is chargeable with radioactive isotopes, and may, in one embodiment, include one or more dissolvable web nettings. These web nettings surround and encircle the at least one seed and, in turn, maintain the at least one seed in a substantially linear arrangement prior to positioning the web nettings about selected ones of the cancerous cells.

The system also includes a seed deployment assembly which locates and delivers the at least one seed, with or without the dissolvable web nettings positioned thereabout, into the tissue of an organism, in and around the cancerous cells. The deployment assembly includes an elongated cannula having a proximal and a distal end. The distal end and the proximal end are opposite one another, and include a conduit positioned therebetween.

Further, the system includes a hub assembly connected to the proximal end of the elongated cannula for staging and directing the at least one seed, with or without the web nettings, through the elongated cannula from the proximal end to the distal end. Consequently, the hub assembly directs the at least one seed (and web nettings if utilized) into the tissue at a desired location near the cancerous cells. Moreover, the system includes an obturator for telescopically projecting the at least one seed (again, with or without the web nettings) through both the hub assembly and the elongated cannula.

In a preferred embodiment, the hub assembly has an initial inner diameter at its proximal end and an operable length between the proximal end of the hub assembly and the proximal end of the cannula. The ratio of the initial inner diameter at the proximal end of the hub assembly, relative to the operable length of the hub assembly, is in the range of 0.075 to 0.175, to preclude release of the at least one seed from the at least one dissolvable web netting and to preclude jamming within the hub assembly of the at least one seed or the at least one seed and at least one dissolvable web netting.

In this embodiment, the hub assembly includes a first conical section having a proximal and a distal end. The first conical section extends from the proximal end to the distal end. Specifically, the first conical section tapers inwardly from the proximal end toward the distal end to define a substantially continuous first slope, which does not exceed 1°30'. Moreover, the first conical section extends from the proximal end of the hub assembly for at least half of the operable length of the hub assembly.

The hub assembly also includes a second, distinct conical section between the distal end of the first conical section and the proximal end of the elongated cannula. The second conical section includes a substantially continuous second slope extending between the distal end of the first conical section and the proximal end of the elongated cannula. In this embodiment, the second slope is not less than 7°30', and the length of the second conical section extends for less than half of the operable length of the hub assembly.

Preferably, the elongated cannula comprises an 18 gauge cannula member and includes a stylus. The stylus is located at the distal end of the elongated cannula, and facilitates insertion of the elongated cannula into the organism's tissue. Further, the elongated cannula includes equidistantly-spaced, radiologically visible markings for denominating divisions of length.

The distal end of the hub assembly telescopically receives and secures the proximal end of the cannula therewithin. In a preferred embodiment, the hub assembly is formed of a plastic material. Additionally, the outer surface of the hub assembly is substantially rectangular.

Preferably, the length of the obturator is at least as long as the collective length of the elongated cannula and hub assembly combined. Further, the obturator has equidistantly-spaced, radiologically visible markings for denominating divisions of length.

BRIEF DESCRIPTION OF THE DRAWINGS

FIG. 1 is a cross-sectional view of the hub assembly according to the prior art;

FIG. 2 is an exploded, perspective view of a portion of the isotope seeding system according to the present invention in which non-netted radioactive seeds have been projected through the cannula;

FIG. 3 is a perspective view of the isotope seeds in the web netting according to one embodiment of the present invention;

FIG. 4 is a cross-sectional view of the hub assembly according to the present invention;

FIG. 5 is an exploded, perspective view of the isotope seeding system according to the present invention; and FIG. 6 is a perspective view of the seeds in the web nettings after insertion into an organism's tissue.

DETAILED DESCRIPTION OF THE DISCLOSURE

While this invention is susceptible of embodiment in many different forms, there is shown in the drawings and will be described herein in detail specific embodiments, with the understanding that the present invention is to be considered as an exemplification of the principles of the invention and is not intended to limit the intention to the embodiments illustrated.

FIG. 1 illustrates a hub assembly for use in an isotope seeding system according to the prior art. As shown in FIGS. 2 and 4, isotope seeding system 20 controls the release of radioactive seeds for the treatment of cancerous cells to preclude against jamming and inadvertent migration of the seeds during cancer treatment procedures, such as prostate cancer surgery. Isotope seeding system 20, in FIG. 2, comprises at least one seed 22a, while in FIG. 3, employs at least one web netting 24, and seed deployment assembly 26. Moreover, seed deployment assembly 26 includes elongated cannula 28, hub assembly 30 and obturator 32.

As shown in FIG. 3, the at least one seed 22 is chargeable with radioactive isotopes, such as iodine or palladium, and placed, in one embodiment, within the at least one web netting 24 to maintain the at least one seed 22 in a substantially rigid, linear arrangement prior to positioning and arrangement of the at least one web netting 24. Such a determination is usually based on factors such as tumor size and location. Notably, the use of iodine, as opposed to palladium, results in reduced radiation exposure to medical personnel, patients and their families. The use of other radioactive isotopes is likewise contemplated. Further, the at least one seed 22 is sterile when shipped.

The at least one seed 22 can be charged with varying dosage strength, which is determined on a case-by-case basis. Accurate dosimetry depends on knowing the number, spacing and individual seed strength required to properly treat the cancerous cells. Moreover, individual seed strength is usually determined through nomogram and computer calculations. As shown in FIG. 6, the at least one seed 22 can be homogeneously distributed about selected ones of cancerous cells to maximize the efficiency of iodine seeding to treat prostate cancer; although use of the at least one web netting 24 is optional inasmuch as the at least one seed 22 can be projected without such netting.

Seed deployment assembly 26, as shown in FIG. 2, is utilized for locating and delivering the at least one seed 22a, or the at least one web netting 24 positioned thereabout (see FIG. 3), into an organism's tissue, proximate to the cancerous cells (see FIG. 6). Elongated cannula 28 includes proximal end 34 and distal end 36. Distal end 36 is opposite proximal end 34, and conduit 38 is positioned therebetween. In a preferred embodiment, elongated cannula 28 comprises an eighteen gauge cannula member. Additionally, as shown in FIGS. 2, 5 and 6, elongated cannula 28 includes stylus 40. Stylus 40 is located at distal end 36 of elongated cannula 28, and facilitates insertion of elongated cannula 28 into the organism's tissue. Elongated cannula 28 further includes equidistantly-spaced markings 42 (see FIG. 2) for denominating divisions of length. Markings 42 are radiologically visible and, in turn, allow the surgeon to determine the depth of elongated cannula 28 at any point during surgery.

Elongated cannula 28 attaches to hub assembly 30 at proximal end 34, and hub assembly 30 stages and directs the at least one seed 22a, with or without the at least one web netting 24 (see FIG. 3), through the elongated cannula 28 from proximal end 34 to distal end 36. Consequently, as shown in FIG. 3, the at least one seed 22 in the at least one web netting 24 may be released into the tissue at a desired location proximate to the cancerous cells. Hub assembly 30 includes proximal end 46 and distal end 47. In a preferred embodiment, distal end 47 telescopically receives and secures proximal end 34 therewithin.

Hub assembly 30 includes initial inner diameter 44 at its proximal end 46, and operable length 38. In a preferred embodiment, initial inner diameter 44 is approximately 0.108 inches. As discussed above, initial inner diameter "a" in the prior art (see FIG. 1) is 0.168 inches. The smaller initial inner diameter 44, assuming the identical operable length 38 in two devices, results in a smaller overall area in which the at least one seed 22a (or the at least one seed 22 with the at least one web netting 24) must travel before entering elongated cannula 28. Consequently, the opportunity for the at least one seed 22 to be released in hub assembly 30, prior to engagement of the cancerous cells, is reduced. Additionally, the opportunity for the at least one seed 22a or 22 to jam within hub assembly 30 is greatly reduced.

As shown in FIG. 4, operable length 38 is the distance between proximal end 46 of hub assembly 30 and proximal end 34 of elongated cannula 28. Moreover, the outer surface of hub assembly 30 is substantially rectangular and hub assembly 30 is formed of a plastic material. In a preferred embodiment, operable length 38 is approximately 0.745 inches. The ratio of initial inner diameter 44 relative to operable length 38 is in the range of 0.075 to 0.175. Preferably, the ratio is approximately 0.14. However, in the prior art device (see FIG. 1), this ratio is 0.23. Substantially lowering this ratio has the effect of increasing the amount of at least one seed 22a or 22 that is released in linear arrangement in and around the cancerous cells during prostate cancer surgery. Further, lowering this ratio has the added effect of preventing jamming of the at least one seed 22a or 22 within hub assembly 30 during such surgery.

In a preferred embodiment, hub assembly 30 includes first conical section 50 which further includes proximal end 54 and distal end 56. First conical section 50 tapers inwardly from proximal end 54 to distal end 56 to define a substantially continuous first slope 58. In this preferred embodiment, first slope 58 does not exceed 1°30', and first conical section 50 extends from proximal end 46 for at least half the distance of operable length 38. Preferably, first slope 58 is approximately 1°.

Additionally, hub assembly 30 includes second conical section 52 which extends between distal end 56 of first conical section 50 and proximal end 34 of elongated cannula 28. Second conical section 52 tapers inwardly from distal end 56 toward proximal end 34 to define a substantially continuous second slope 60. In the preferred embodiment, second slope 60 exceeds 7°30'. Ideally, second slope 60 is approximately 8°.

Obturator 32 is inserted into proximal end 46 and telescopically projects the at least one seed 22a, or the at least one seed 22 and at least one web netting 24 through both hub assembly 30 and elongated cannula 28. In a preferred embodiment, the length of obturator 32 is at least as long as the collective length of elongated cannula 28 and hub assembly 30 combined. Moreover, as shown in FIG. 2, obturator 32 includes equidistantly-spaced markings 33 (see FIG. 2) for denominating divisions of length. Markings 33 are radiologically visible and, in turn, allow the surgeon to determine the location of obturator 32 at any point during surgery.

In operation, it must be determined how many of the at least one seed 22a and/or the at least one seed 22 and at least one web netting 24, are to be used in the cancer treatment procedure. Once determined, the seeds, with or without the web netting, are inserted into hub assembly 30. As shown in FIG. 6, stylus 40 of elongated cannula 28 is then inserted into the organism's tissue, near the cancerous cells. Markings 42 allow the surgeon to determine the exact depth of elongated cannula 28 into an organism's tissue, and thus, the position of stylus 40 relative to the cancerous cells.

In FIG. 5, obturator 32 guides the at least one seed 22 and the at least one web netting 24 through both hub assembly 30 and elongated cannula 28. Obturator 32 can be retracted towards the proximal end 46 of hub assembly 30, which results in a tightening of the at least one seed 22 and the at least one web netting 24. Consequently, seed deployment assembly 26 is guided to its predetermined position within the prostate under direct ultrasound visualization. Once properly positioned, seed deployment assembly 26 is withdrawn, leaving in the tissue the at least one seed 22a, or the at least one seed 22 and at least one web netting 24, in a linear fashion from base to apex of the cancerous cells.

After the at least one seed 22 (and, optionally, the at least one web netting 24 have been implanted), the at least one seed 22 that have migrated may be removed, reloaded and reimplanted, usually into the most concentrated area of cancerous cells where netting is used. The at least one web netting 24 dissolves and the at least one seed 22 encircles the cancerous cells. Subsequently, the at least one seed 22 destroys the cancerous cells.

The foregoing description and drawings merely explain and illustrate the invention, and the invention is not limited thereto except insofar as the appended claims are so limited, as those skilled in the art who have the disclosure before them will be able to make modifications and variations therein without departing from the scope of the invention.

We claim:

1. An isotope seeding system that controls the release of radioactive seeds for treatment of cancerous cells to preclude against jamming and inadvertent migration of said radioactive seeds curing cancer treatment procedures, said system comprising:

at least one seed that is chargeable with radioactive isotopes;

a seed deployment assembly for locating and delivering said at least one seed into the tissue of an organism, proximate to said cancerous cells;

said deployment assembly including an elongated cannula having a proximal and a distal end, said distal end opposite said proximal end and a conduit positioned therebetween;

a hub assembly attached to the elongated cannula at the proximal end of said cannula, the hub assembly including a proximal and distal end, and an interior region, said distal end of said hub assembly operably associated with the proximal end of said elongated cannula for staging and directing said at least one seed through said elongated cannula from said cannula proximal end to said cannula distal end and, in turn, into said tissue at a desired location proximate said cancerous cells;

an obturator for telescopic projection of said at least one seed through both said hub assembly and said elongated cannula; and said hub assembly having an initial inner diameter at its proximal end and an operable length between said proximal end of said hub assembly and said proximal end of said cannula, said ratio of said initial inner diameter at the proximal end of said hub assembly, relative to the operable length of said hub assembly, being in the range of 0.075 to 0.175, to ensure against the inadvertent migration and jamming of said at least one seed in said hub assembly; and the interior region of said hub assembly including a first substantially conical section having a length and a second substantially conical section having a length, the length of the first conical section being at least 50% of the combined length of the first and second conical sections.

2. The invention of claim 1 in which said system further comprises at least one dissolvable web netting operably associated with and positioned about said at least one seed for housing and maintaining the at least one seed in a substantially linear arrangement prior to positioning and arrangement of said at least one dissolvable web netting and, in turn, said at least one seed positioned therewithin, about selected ones of said cancerous cells, said seed deployment assembly further locating and delivering said at least one seed and said at least one dissolvable web netting positioned thereabout into said organism's tissue, proximate to said cancerous cells, in which both said at least one seed and at least one dissolvable web netting are staged and directed through said hub assembly by said obturator towards the projected release of both from the distal end of said elongated cannula.

3. The system according to claim 1 wherein the first substantially conical section includes a first conical proximal and distal end, said first conical section tapering inwardly from said first conical proximal end to said first conical distal end, and the second, distinct substantially conical section operably positioned between said distal end of said first conical section and said proximal end of said elongated cannula, said first conical section tapering inwardly from said first conical proximal end toward said first conical distal end to define a substantially continuous first slope, said first slope not exceeding 1°30'.

4. The system according to claim 3 wherein the first conical section extends from said proximal end of said hub assembly for at least half of the operable length of said hub assembly.

5. The system according to claim 3 wherein the second conical section includes a substantially continuous second slope tapering inwardly between said distal end of said first conical section and said proximal end of said elongated cannula, said second slope not less than 7°30'.

6. The system according to claim 5 wherein said length of said second conical section extends for less than half of the operable length of said hub assembly.

7. The system according to claim 1 wherein said elongated cannula comprises an 18 gauge cannula member.

8. The system according to claim 1 wherein said elongated cannula includes a stylus, said stylus being positioned at the distal end of said elongated cannula, said stylus facilitates insertion of the elongated cannula into said organism's tissue.

9. The system according to claim 1 wherein the distal end of said hub assembly telescopically receives and secures the proximal end of said cannula therewithin.

10. The system according to claim 1 wherein the elongated cannula includes equidistantly-spaced, radiologically visible markings for denominating divisions of length.

11. The system according to claim 1 wherein the obturator includes equidistantly-spaced, radiologically visible markings for denominating divisions of length.

12. The system according to claim 1 wherein the length of the obturator is at least as long as the collective length of said elongated cannula and said hub assembly.

13. The system according to claim 1 wherein the outer surface of said hub assembly is substantially rectangular.

14. The system according to claim 1 wherein the hub assembly is formed of a plastic material.

15. The system according to claim 1 wherein said hub assembly has an initial inner diameter at its proximal end and an operable length between said proximal end of said hub assembly and said proximal end of said cannula, said ratio of said initial inner diameter at the proximal end of said hub assembly, relative to the operable length of said hub assembly, being in the range of 0.075 to 0.175, to ensure against the inadvertent migration and jamming of said at least one seed in said hub assembly.

16. The system according to claim 1 wherein the length of the first substantially conical section ranges between 75% to 85% of the combined length of the first and second conical sections.

* * * * *